(12) United States Patent
Wang et al.

(10) Patent No.: US 7,053,752 B2
(45) Date of Patent: *May 30, 2006

(54) GENERAL PURPOSE DISTRIBUTED OPERATING ROOM CONTROL SYSTEM

(75) Inventors: Yulun Wang, Goleta, CA (US); Charles S. Jordan, Santa Barbara, CA (US); Darrin R. Uecker, Santa Barbara, CA (US); Charles C. Wooters, Goleta, CA (US)

(73) Assignee: Intuitive Surgical, Sunnyvale, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 10/666,922

(22) Filed: Sep. 18, 2003

(65) Prior Publication Data

US 2004/0124964 A1 Jul. 1, 2004

Related U.S. Application Data

(63) Continuation of application No. 08/693,352, filed on Aug. 6, 1996, now Pat. No. 6,646,541.

(51) Int. Cl.
*G10L 3/00* (2006.01)

(52) U.S. Cl. ......................... 340/3.54; 704/275; 606/1; 700/258

(58) Field of Classification Search ............... 340/3.54, 340/3.5, 3.7, 825.52; 600/101, 589, 539, 600/118; 606/1; 608/425; 367/198; 381/110; 704/226, 270, 275; 700/258
See application file for complete search history.

(56) References Cited

U.S. PATENT DOCUMENTS

| | | |
|---|---|---|
| 977,825 A | 12/1910 | Murphy |
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,158,750 A | 6/1979 | Sakoe et al. |
| 4,207,959 A | 6/1980 | Youdin et al. |
| 4,216,462 A | 8/1980 | McGrath et al. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |

(Continued)

FOREIGN PATENT DOCUMENTS

DE 9204118.3 7/1992

(Continued)

OTHER PUBLICATIONS

ABSTRACT of a presentation "3-D Vision Technology Applied to Advanced Minimally Invasive Surgery Systems" given at the 3rd World Congress of Endoscopic Surgery in Bordeaux, Jun. 18-20, 1992 (1 page total).

(Continued)

*Primary Examiner*—Edwin C. Holloway, III

(57) ABSTRACT

The present invention pertains to control systems and provides a run time configurable control system for selecting and operating one of a plurality of operating room devices from a single input source, the system comprising a master controller having a voice control interface and means for routing control signals. The system additionally may include a plurality of slave controllers to provide expandability of the system. Also, the system includes output means for generating messages to the user relating to the status of the control system in general and to the status of devices connected thereto.

13 Claims, 4 Drawing Sheets

U.S. PATENT DOCUMENTS

| | | |
|---|---|---|
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,750,136 A | 6/1988 | Arpin et al. |
| 4,762,455 A | 8/1988 | Coughlan et al. |
| 4,776,016 A | 10/1988 | Hansen |
| 4,791,934 A | 12/1988 | Brunnett |
| 4,791,940 A | 12/1988 | Hirschfeld et al. |
| 4,794,912 A | 1/1989 | Lia |
| 4,807,273 A | 2/1989 | Haendle |
| 4,815,006 A | 3/1989 | Andersson et al. |
| 4,815,450 A | 3/1989 | Patel |
| 4,817,050 A | 3/1989 | Komatsu |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,023 A | 7/1993 | Nakano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,274,862 A | 1/1994 | Palmer, Jr. et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,335,313 A | 8/1994 | Douglas |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,372,147 A | 12/1994 | Lathrop, Jr. et al. |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,436,542 A | 7/1995 | Petelin et al. |
| 5,442,728 A | 8/1995 | Kaufman et al. |
| 5,443,384 A | 8/1995 | Kirsch et al. |
| 5,445,166 A | 8/1995 | Taylor |
| 5,451,924 A | 9/1995 | Massimino et al. |
| 5,455,766 A | 10/1995 | Schaller et al. |
| 5,458,547 A | 10/1995 | Teraoka et al. |
| 5,458,574 A | 10/1995 | Machold et al. |
| 5,476,010 A | 12/1995 | Fleming et al. |
| 5,482,073 A | 1/1996 | Strum |
| 5,490,117 A | 2/1996 | Oda et al. |
| 5,490,843 A | 2/1996 | Hildwein et al. |
| 5,500,854 A | 3/1996 | Uotila |
| 5,506,912 A | 4/1996 | Nagasaki et al. |
| 5,511,256 A | 4/1996 | Capaldi |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,566,272 A | 10/1996 | Brems et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,627,584 A | 5/1997 | Nishikori et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,640,953 A | 6/1997 | Bishop et al. |

| | | |
|---|---|---|
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,713,350 A | 2/1998 | Yokota et al. |
| 5,715,548 A | 2/1998 | Weismiller et al. |
| 5,715,823 A | 2/1998 | Wood |
| 5,718,038 A | 2/1998 | Takiar et al. |
| 5,727,569 A | 3/1998 | Benetti et al. |
| 5,729,659 A | 3/1998 | Potter |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,771,511 A | 6/1998 | Kummer et al. |
| 5,774,741 A | 6/1998 | Choi |
| 5,774,841 A | 6/1998 | Salazar et al. |
| 5,776,126 A | 7/1998 | Wilk et al. |
| 5,779,623 A | 7/1998 | Bonnell |
| 5,788,688 A | 8/1998 | Bauer et al. |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,802,467 A | 9/1998 | Salazar et al. |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,809,591 A | 9/1998 | Capaldi et al. |
| 5,810,880 A | 9/1998 | Jensen et al. |
| 5,812,978 A | 9/1998 | Nolan |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,836,869 A | 11/1998 | Kudo et al. |
| 5,841,950 A | 11/1998 | Wang et al. |
| 5,842,173 A | 11/1998 | Strum et al. |
| 5,844,824 A | 12/1998 | Newman et al. |
| 5,855,583 A | 1/1999 | Wang et al. |
| 5,857,967 A | 1/1999 | Frid et al. |
| 5,859,934 A | 1/1999 | Green |
| 5,860,995 A | 1/1999 | Berkelaar |
| 5,876,325 A | 3/1999 | Mizuno et al. |
| 5,877,819 A | 3/1999 | Branson |
| 5,878,193 A | 3/1999 | Wang et al. |
| 5,882,206 A | 3/1999 | Gillio |
| 5,884,350 A | 3/1999 | Kurze |
| 5,887,121 A | 3/1999 | Funda et al. |
| 5,895,461 A | 4/1999 | De La Huerga |
| 5,897,498 A | 4/1999 | Canfield et al. |
| 5,924,074 A | 7/1999 | Evans |
| 5,931,832 A | 8/1999 | Jensen |
| 5,950,629 A | 9/1999 | Taylor et al. |
| 5,970,457 A | 10/1999 | Brant et al. |
| 5,971,976 A | 10/1999 | Wang et al. |
| 6,024,695 A | 2/2000 | Taylor et al. |
| 6,080,181 A | 6/2000 | Jensen et al. |
| 6,102,850 A | 8/2000 | Wang et al. |
| 6,201,984 B1 | 3/2001 | Liang et al. |
| 6,224,542 B1 | 5/2001 | Chang et al. |
| 6,278,975 B1 | 8/2001 | Brant et al. |
| 6,463,361 B1 | 10/2002 | Wang et al. |
| 6,496,099 B1 | 12/2002 | Wang et al. |
| 6,642,836 B1 * | 11/2003 | Wang et al. ............... 340/3.54 |
| 6,646,541 B1 | 11/2003 | Wang et al. |

FOREIGN PATENT DOCUMENTS

| | | |
|---|---|---|
| DE | 4310842 | 1/1995 |
| EP | 0239409 A1 | 9/1987 |
| EP | 424687 | 5/1991 |
| EP | 776738 | 6/1997 |
| FR | 2 642 882 | 8/1990 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 96/09587 | 3/1996 |
| WO | WO 97/15240 | 5/1997 |
| WO | WO 98/25666 | 6/1998 |
| WO | WO 99/21165 | 4/1999 |
| WO | WO 99/42029 | 8/1999 |

OTHER PUBLICATIONS

ABSTRACT of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

ABSTRACT of a presentation given at the 3rd World Congress of Endoscopic Surgery in Bordeaux (Jun. 18 to 20, 1992), entitled "Session 15/2" (1 page total).

ABSTRACT of a presentation given at the 3rd World Congress of Endoscopic Surgery in Bordeaux (Jun. 18 to 20, 1992), entitled "Session 15/4" (1 page total).

ABSTRACT of a presentation given at the 3rd World Congress of Endoscopic Surgery in Bordeaux (Jun. 18 to 20, 1992), entitled "Session 15/5" (1 page total).

ABSTRACT of a presentation given at the 3rd World Congress of Endoscopic Surgery in Bordeaux, Jun 18-20, 1992, entitled "Session 15/1" (1 page total).

Bejczy, "Controlling Remote Manipulators through Kinesthetic Coupling," Computers in Mechanical Engineering 1983, pp. 48-60.

Besant et al., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).

Charles et al., "Design of a Surgeon-Machine Interface for Teleoperated Microsurgery," IEEE 1989 (3 pages total).

Colgate, "Power and Impedance Scaling in Bilateral Manipulation," IEEE, 1991, pp. 2292-2297.

Corcoran, "Robots for the Operating Room," The New York Times, Sunday Jul. 19, 1992, Section 3, p. 9, col. 1 (2 pages total).

Das et al., "Kinematic Control and Visual Display of Redundant Teleoperators," IEEE 1989 pp. 1072-1077.

Dolan et al., "A Robot in an Operating Room: A Bull in a China Shop," IEEE, 1987, pp. 1096-1097.

Gayed et al., "An Advanced Control Micromanipulator for Surgical Applications," Systems Science vol. 13, 1987, pp. 23-24.

Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).

Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).

Green, Statutory Declaration of Dr. Philip S. Green, presenter of the video entitled "Telepresence Surgery—The Future of Minimally Invasive Medicine" (32 pages total).

Guerrouad, "Voice Control in the Surgery Room," IEEE Engineering in Medicine & Biology Society 11th Annual International Conference 1989 (2 pages total).

Guerrouad et al., "S.M.O.S.: Stereotaxical Microtelemanipulator for Ocular Surgery," IEEE, 1989, pp. 879-880.

Inque et al., "Six-axis Bilateral Control of an Articulated Slave Manipulator Using a Cartesian Master Manipulator," Advanced Robotics, 4, No. 2, 1990, pp. 139-150.

Kazerooni, "Human/Robot Interaction via the Transfer of Power and Information Signals—Part I: Dynamics and Control Analysis," IEEE, 1989, pp. 1632-1640.

Kazerooni, "Human/Robot Interaction via the Transfer of Power and Information Signals—Part II: An Experimental Analysis," IEEE, 1989, pp. 1641-1647.

Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).

Lavallee, "A New System for Computer Assisted Neurosurgery," IEEE, 1989, vol. 11, pp. 926-927.

Mair, Industrial Robotics, Prentice Hall, 1988, pp. 41-43, 49-50, 54, 203-209.

Majima et al., "On a Micro-Manipulator for Medical Application—Stability Consideration of its Bilateral Controller," Mechatronics, 1991, pp. 293-309.

Nasa, "Anthropomorphic Remote Manipulator", NASA Tech Briefs, 1991 (1 page total).

Preising et al., "A Literature Review: Robots in Medicine," IEEE Jun. 1991, pp. 13-22 & 71.

Sabatini et al., "Force Feedback-Based Telemicromanipulation for Robot Surgery on Soft Tissues," IEEE, 1989, pp. 890-891.

Taubes, "Surgery in Cyberspace," Discover Magazine, Dec. 1994, pp. 85-92.

Taylor et al., "Taming the Bull: Safety in a Precise Surgical Robot," IEEE, 1991, pp. 865-871.

Tejima, "A New Microsurgical Robot System for Corneal Transplantation," Precision Machinery, 1988 vol. 2, pp. 1-9.

Tendick et al., "Analysis of the Surgeon's Grasp for Telerobotic Surgical Manipulation," IEEE, 1989, pp. 914-915.

Thring, "Robots and Telechirs: Manipulator with Memory: Remote Manipulators: Machine Limbs for the Handicapped," Wiley & Sons, 1983 (26 pages total).

Transcript of a video presented by SRI at the 3rd World Congress of Endoscopic Surgery in Bordeaux on Jun. 18-20, 1992, in Washington on Apr. 9, 1992, and in San Diego, CA on Jun. 4-7, 1992 entitled "Telepresence Surgery—The Future of Minimally Invasive Medicine" (3 pages total).

Trevelyan et al., "Motion Control for a Sheep Shearing Robot," Proceedings of the 1st International Symposium on Robotics Research, MIT, Cambridge, Massachusetts, USA, 1983, pp. 175.

Vibet, "Properties of Master-Slave Robots," Motor-con, 1987, pp. 309-314.

Wolf et al., "Student Reference Manual for Electronic Instrumentation Laboratories," Prentice Hall, New Jersey 1990, pp. 498 and 499.

Stryker Endoscopy, "Sidne," Operating and Maintenance Manual, 33 total.

Wilson et al., "Filmless PACS in a multiple facility environment," Proceedings of the Spie, Spie, Bellingham, VA, US, vol. 2711, pp. 500-509 (XP002082137).

ABSTRACT of a presentation "Concept and Experimental Application of a Surgical Robot System and Steerable MIS Instrument SMI" given at the $3^{rd}$ World Congress of Endoscopic Surgery in Bordeaux, Jun. 18-29, 1992 (1 page total).

Alexander, "A Survey Study of Teleoperators, Robotics, and Remote Systems Technology", Remotely Manned Systems-Exploration and Operation in Space, California Institute of Technology 1973.

Alexander, "Impacts of Telemation on Modern Society", On the Theory and Practice of Robots and Manipulators vol. II, 1974.

Fu et al., "Robotics: Control, Sensing, Vision and Intelligence", Table of Contents, McGraw—Hill Book Company, 1987.

Rasor et al., "Endocorporeal Surgery Using Remote Manipulators", Remotely Manned Systems—Exploration and Operation in Space, California Institute of Technology 1973.

* cited by examiner

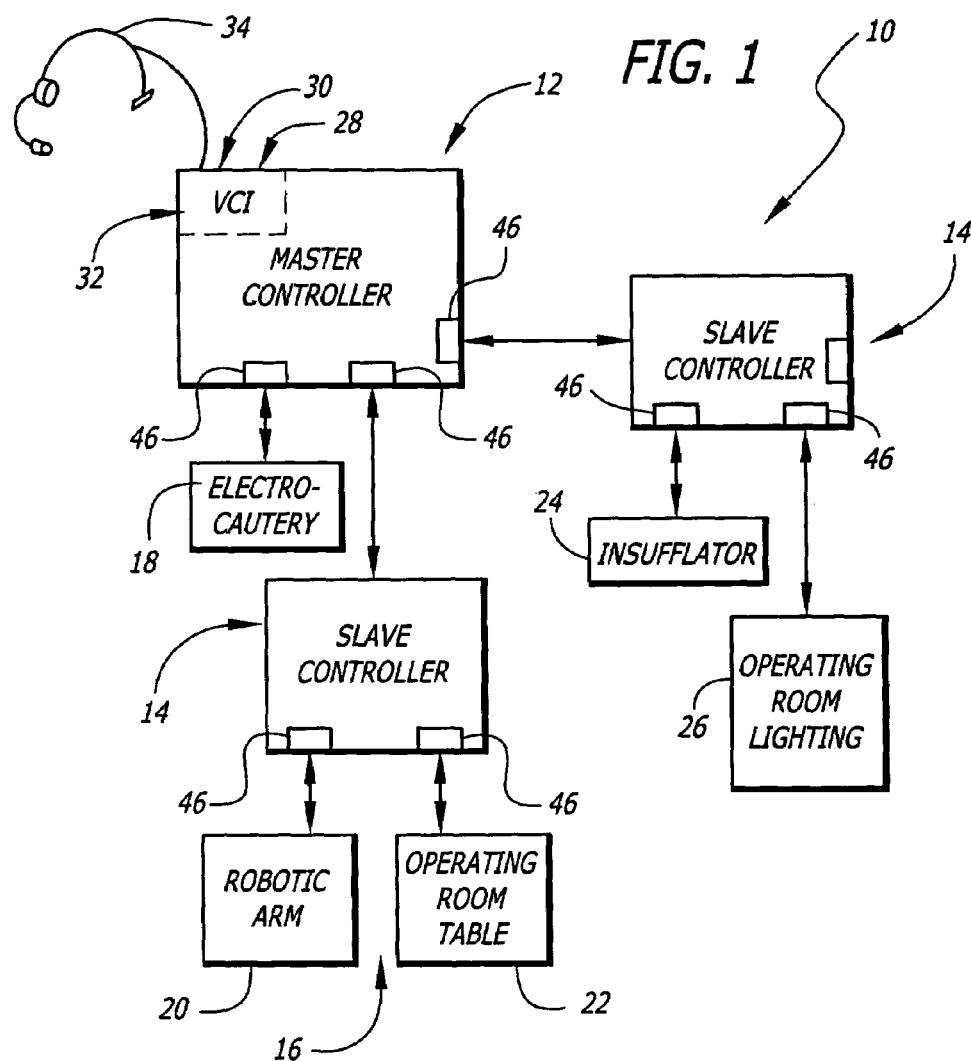
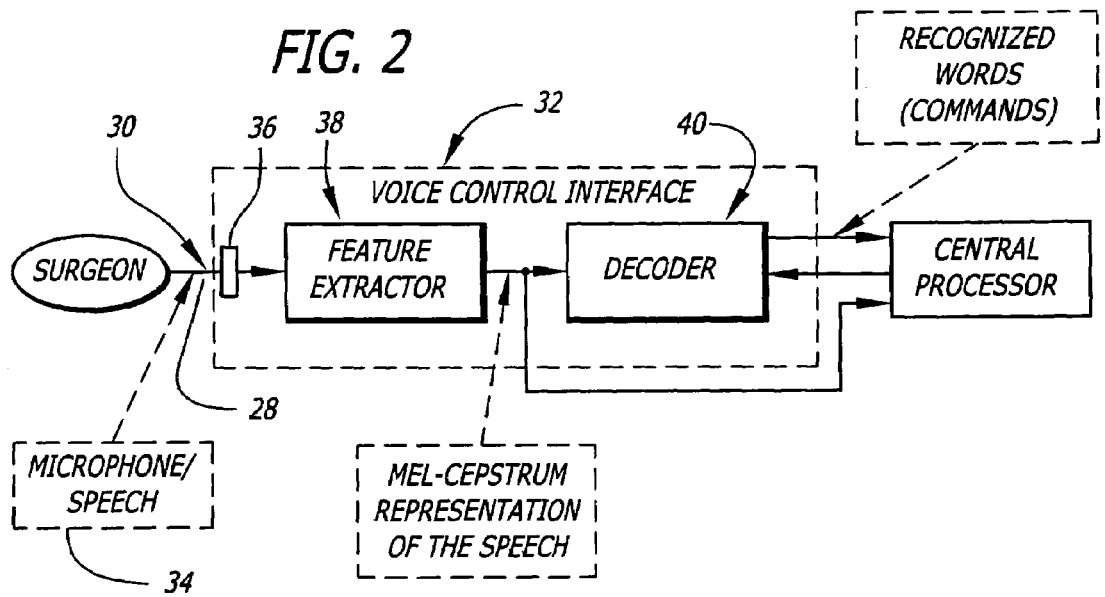

GENERAL PURPOSE DISTRIBUTED OPERATING ROOM CONTROL SYSTEM

CROSS-REFERENCE TO RELATED APPLICATION

This is a continuation patent application which claims priority from U.S. patent application Ser. No. 08/693,352 filed Aug. 6, 1996, now U.S. Pat. No. 6,646,541 the full disclosure of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

1. Field of the Invention

The present invention generally relates to control systems. More particularly, the present invention relates to a control system and apparatus that allows multiple surgical devices to be controlled from one or more input devices. Even more particularly, the present invention provides a run-time configurable control system allowing operating room component connectivity and control.

2. Description of Related Art

Many surgical procedures are performed with multiple instruments. For example, some laproscopic procedures are performed utilizing a robotic arm system produced by Computer Motion, Inc. of Goleta, Calif. to hold and move an endoscope. The surgeon may also use a laser to cut tissue, an electrocautery device to cauterize the tissue, and lights to illuminate the surgical site.

Each instrument has a unique control interface for its operation. Therefore, the surgeon must independently operate each device. For example, the surgeon must utilize a foot pedal to control the electrocautery device, a separate foot pedal to operate the robotic arm, and yet another interface to operate the laser.

Operating multiple devices may distract the surgeon, thereby reducing the efficiency of performing various procedures. Additionally, it is cumbersome utilizing various devices where each device has a separate user interface. If a new device is introduced into the operating room environment, the doctor must learn how to use the new user interface. Additionally, there is currently no known run time configurable system for operating more than one specific operating room device via voice control. As such, if there are two or more devices in the operating room that are voice controlled, the doctor has to remove the microphone used for one device and replace it with the microphone for the other device. Obviously, this creates many problems associated with productivity. Additionally, the necessity of actually switching between many user interfaces takes a measurable amount of time and as such, extends the time that a patient is under anesthesia, which may add to the danger of a procedure.

Therefore, what is needed in the art is a general purpose platform for controlling a plurality of devices such that devices can be added or subtracted from the platform depending upon the environment into which the platform, also known as a control system is introduced. The system may additionally be automatically configured at start up. Additionally, what is needed is a system and method for selecting and operating one of the plurality of the attached devices, namely operating room devices. It is to the solution of the hereinabove mentioned problems to which the present invention is directed.

BRIEF SUMMARY OF THE INVENTION

In accordance with the present invention there is provided a control system for selecting from and controlling a plurality of devices in an operating room, the control system comprising:

a master controller, the master controller comprising:

means for receiving selection commands from a user wherein each selection command is associated with one specific device in electrical communication with the master controller;

means for receiving control commands from a user;

means for converting selection commands and control commands into corresponding selection signals and control signals;

d) means for routing control signals to a device specified by a selection command received by the means for receiving selection commands.

In accordance with a first aspect of the present invention, there is provided a master controller for selecting and controlling a plurality of devices. Each of the plurality of devices to be controlled are in electrical communication or in wireless communication with the master controller, either directly or via a slave controller which will be discussed in more detail hereinbelow with respect to the second aspect of the present invention.

The master controller includes means for receiving selection commands issued by a user. The selection commands available to the user are based upon the devices in electrical communication with the master controller. The master controller may recognize those devices that are in electrical communication therewith upon startup of the master controller. This will be described in detail in the description of the preferred embodiment. Each device in electrical communication with the master controller is represented by a correspondingly available selection command.

The master controller additionally includes means for receiving control commands from the user. Both the means for receiving selection commands and the means for receiving control commands from a user may be included in a voice control interface (VCI) for receiving voice commands. The system may additionally employ a foot pedal, a hand held device, or some other device which receives selection or control commands or inputs indicative of such commands from a user. The VCI provides signals indicative of a user's selection of a specific device and signals indicative of control commands the user wishes to supply to the device specified by a specific selection command. These are known, respectively, as selection signals and control signals. If the user is using a foot pedal, hand controller or some other input device, the VCI is not utilized as the inputs are already in the form of electrical signals as opposed to voice input. Alternatively, a combination of devices may be used to receive selection and control commands and to provide selection and control signals indicative of such commands.

The master controller additionally includes means for routing control signals to a device specified by a selection command. For example, if the user wants to operate the laser, device used in many surgeries and contemplated as being included as one of the devices that may be operated via the control system of the present invention, then the user may issue a selection command indicating such, i.e. speak the word "laser" or the words "select laser". As such, the name of the device may serve as the selection command, or the selection command may be the combination of two or more words.

Subsequent to receiving a selection command from the user and converting the selection command into a selection signal, if necessary, the master controller then routes control commands, or control signals for a selected device indicative of control commands received from the user to the device specified by the preceding selection command. In this exemplary instance, control signals would be routed to the laser. Preferred structures for both selection commands and control commands are disclosed herein in the detailed description of the preferred embodiment of the present invention.

Additionally, a controller may include means for ensuring that control signals indicative of control commands issued subsequent to the receipt of a selection command are, in fact, valid control signals. This is accomplished via a database of valid control commands and grammars that are either prestored in the master, or are prestored in a slave prior to or at system startup which is described hereinbelow.

A second aspect of the present invention is at least one slave electrically connected to the master controller. Each slave controller connected to the master controller operates similarly to the master controller for specific devices electrically connected thereto; additionally, the slave controllers may receive control commands directly from the user if they are to be used as a stand alone unit. However, if they are utilized as slaves then control commands are received at the master controller and converted into control signals and transmitted from the master controller to the slave controller that has the device specified by the last selection command received by the master controller connected thereto. This allows the control system of the present invention to operate with a plurality of different devices without the master controller requiring any knowledge of the devices connected to the slave controllers prior to startup of the control system.

The slave controllers are connected to the master controller just like any other device; however, each slave controller provides the master controller information relating to the specific devices that are connected thereto, so the master controller, generally at startup, is provided information as to exactly what devices are connected to the system. The selection commands available to the user include all devices connected to each of the slave controllers as well as the devices directly connected to the master controller.

By providing an open architecture such as that generally set out hereinabove, and more particularly, a master controller and slave controllers, various devices may be controlled from a single controller, or a plurality of controllers, such that a doctor utilizing the control system will not have to switch between different control systems or interfaces, or at a minimum will have an easier interface to control each of the devices. It is additionally envisioned that the main means for selecting and controlling each of the devices will be a voice recognition system which will be described in detail hereinbelow.

Also, the control system may include audio and video outputs which are capable of alerting the user to errors in selecting, or controlling specific devices. The audio and video outputs may additionally be used to alert the user to problems with each of the specific devices as well as to provide status notices as to which device(s) are available, which devices are active, as well as a host of other device operation information which will be discussed further hereinbelow.

For a more complete understanding of the present invention, reference is made to the following detailed description and accompanying drawings. In the drawings, like reference characters refer to like parts, in which:

BRIEF DESCRIPTION OF THE DRAWINGS

FIG. 1 is a block diagram of a master controller in electrical communication with both slave controllers and operating room devices in accordance with the present invention;

FIG. 2 is a block diagram of the voice control interface in accordance with the present invention;

DETAILED DESCRIPTION OF THE INVENTION

Figure 3:
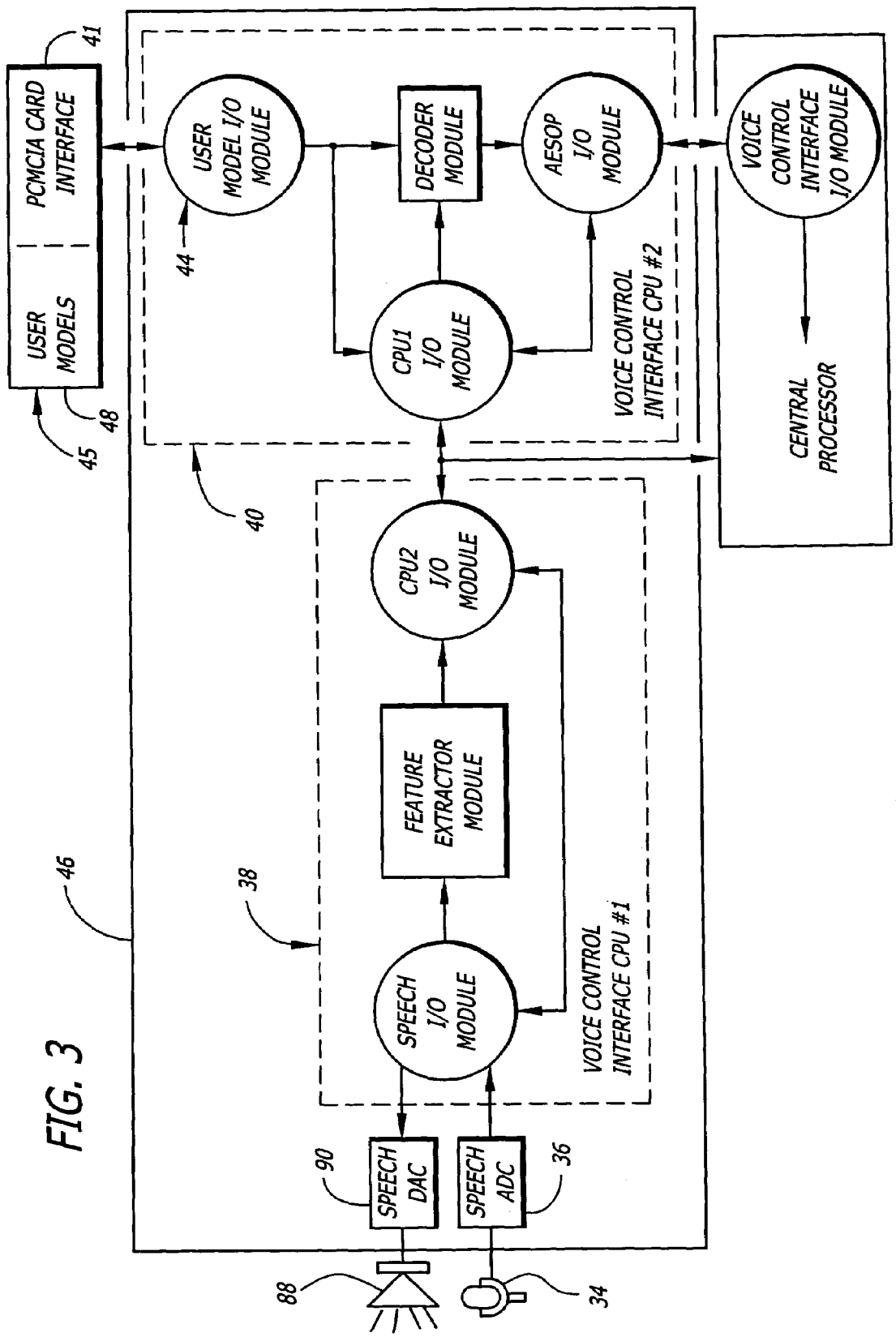
FIG. 3 is a schematic of the voice control interface card in accordance with the present invention.

In accordance with the present invention, there is shown in FIG. 1 an operating room control system, generally at 10, in accordance with the present invention. The operating room control system, or control system 10, generally comprises a master controller 12, which is preferably attached to at least one slave controller 14. Although the exemplary preferred embodiment is shown as having both a master controller 12 and at least one slave controller 14 in electrical communication therewith, the control system 10 may be implemented with only a master controller 12 as will be described hereinbelow.

The master controller 12 is electrically connected to and in electrical communication with a plurality of devices 16 via a plurality of communication ports 46. Alternatively, the master controller 12 may be connected to any slave or specific medical device via wireless communications systems such as IR or RF signal transmitters and receivers on each of the master 12, slaves 14, and devices 16. Some of these devices 16 may be at least one slave controller 14 the operation of which will be described hereinbelow. Other devices that are intended to be electrically connected to the master controller 12, either directly or via the at least one slave controller 14 include devices that are commonly found in an operating room environment.

For purposes of non-limiting example, directly connected to the master controller 12 in FIG. 1 is an electrocautery device 18. A robotic arm 20 for holding and manipulating an endoscope, such as that produced by Computer Motion of Goleta, Calif. and marketed under the tradename AESOP is electrically connected with the master controller 12 via one of the at least one slave controllers 14. Also in electrical communication with the master controller 12 via a slave controller is an operating room table 22, an insufflator 24, and an operating room lighting system 26. It is envisioned that any electrically controlled device utilized in an operating room environment may be attached to the master controller 12 either directly or via one of the at least one slave controllers 14.

The master controller 12 is configured to provide a main user interface for each of the devices electrically connected thereto. As such, a doctor can manipulate the operating room environment in a simpler and more direct fashion. Currently, each device in an operating room includes a separate interface. The proximity of the doctor to each interface requires a substantial amount of movement either on the part of the doctor or a nurse to effectuate changes required by the doctor during a medical procedure.

For example, if the doctor needs the lights dimmed slightly, then a nurse currently has to approach the lighting system of the operating room and dim the lights. It would be highly advantageous for the doctor to be able to control such changes directly to keep movement in the operating room to a minimum to increase sterility, and because direct control by the doctor of the operating room environment and the devices he or she is using ensures the highest degree of safety with the smallest amount of error due to miscommunication between people in the operating room. Minimization of movement in an operating room environment is additionally advantageous to reduce the risk of contamination of specific sterile instruments, as well as the operative site itself.

To effectuate such a control system 10, the master controller 12 generally comprises a voice control interface (VCI) 32. The VCI 32 includes means 28 for receiving selection commands from a user wherein each selection command is associated with one specific device in electrical communication with the master controller 12. This is accomplished by providing the master controller 12 a list of the devices that are in electrical communication therewith upon start-up of the control system 10. The process and hardware for providing the master controller 12 with such a list will be described hereinbelow.

As shown in FIG. 2, The VCI 32 additionally comprises means 30 for receiving control commands from a user. In the preferred embodiment, both the means 28 for receiving selection commands and the means 30 for receiving control commands may coexist in the VCI 32 as a microphone 34, for receiving the actual speech of the user, an analog to digital converter 36 for converting the analog speech into a digital representation thereof, a feature extractor 38 for converting the digital representation to a digital representation that is suited for decoding, and a decoder 40 for comparing the features of the transformed digital representation of the speech to a set of presaved user-models 41 to determine whether the speech received at the microphone 34 was a selection command, a control command, or some other speech to be ignored by the master controller 12. Such "other speech" would include extraneous noise, speech between the doctor and another person in the operating suite, as well as speech of other people in the operating suite in general.

Feature extractors, such as the one employed in the present invention, are well known in the art of voice recognition. Feature vectors are preferably generated by the feature extractor 38 utilizing techniques such as Mel-Cepstrum, or linear prediction. It is to be appreciated that such techniques are well-known and are employed in the feature extractor 38 to develop feature vectors that represent speech received by the VCI 32.

Additionally, voice software is also available that provides extractors and decoders such as the ones set out in the present application. As such, although a specific implementation is presented herein for voice recognition, it may be carried out by the inclusion of a pre-made voice recognition system that is purchased from a vendor such as Creative labs under the tradename VOICE BLASTER, Dragon Dictate produced by Dragon Systems, or VOICE PAD produced by Kurzweil AI of Massachusetts, each of these companies produce front-end voice recognition systems.

The decoder 40 utilizes the information produced by the feature extractor 38, by matching the stored user models 41 to the output of the feature extractor 38 utilizing a well-known method, such as a Hidden Markov Modeling. One Hidden Markov Model (HMM) is created for each phoneme. The HMMs are trained to identify their respective phonemes given the Mel-Cepstrum output from the feature extractor 38. The use of Hidden Markov Models for voice recognition is generally well known.

The stored user models 41 used by the decoder 40 may be placed in a memory 44 associated with the VCI itself. As depicted in FIG. 3, such a memory 44 may be incorporated onto a VCI board 46 as an EPROM, a PROM or some other programmable memory storage device. However, it is preferable to store the models on a transportable memory device 45, such as a disk, transportable storage medium or the like. It is even more preferable that the transportable memory device be a PCMCIA format card 48 as data transfer times are reduced and the ruggedness of the system is increased. PCMCIA format cards retain data better than floppy disks. Additionally, the configuration of currently produced PCMCIA cards allows for additional program data to be stored on the PCMCIA format card and downloaded into the master controller 12 when system changes are made (i.e. upgrades to the system software etc.). Therefore, the use of such a PCMCIA form factor card is preferable in the control system 10 of the present invention.

FIG. 3 depicts, in more detail, the VCI 32. Once the user's speech has been digitized at the A/D converter 36, it is fed to the feature extractor 38. The feature extractor 38 functions as set out hereinabove. In more detail, the feature extractor 38 converts the digitized signal into a representation that is suitable for decoding (e.g. Mel-Cepstrum). This representation is then passed to the decoder 40 which compares the representations produced at the feature extractor 38 to the models stored on a memory 44 which contains the user models 41. The memory 44 may be supplied the models 41 via a downloading process from the transportable memory device 45. The models stored in the memory 44 constitute a lexicon, which is the entire set of valid pronunciations, or all of the valid words that the master 12 is to recognize. Because the lexicon is stored on a transportable data storage medium 41, the lexicon may be added to or subtracted from depending upon the devices that are to be connected to the master controller 12. In this fashion, if new equipment is purchased at a date subsequent to the purchase of the master controller 12, then new words may be added to the lexicon through a well-known data acquisition technique, wherein the user speaks the words that are to be added to the lexicon and they are used to update the user models 41 on the transportable memory 45.

Most preferable to the implementation of the present system 10, there is provided one master controller 12 and at least one slave 14 controller. In such a configuration, which will be discussed in more detail hereinbelow, once the master controller or master 12 receives a selection command, all speech received at the VCI 32 of the master 12 that is not a new selection command is fed to the feature extractor of the appropriately attached slave 14. In this way, a plurality of devices may be attached to several different controllers and the lexicon stored in each controller does not have to be downloaded into the master 12. The master 12 only contains the lexicon of all the devices that may be connected to the system 10 as well as the lexicon for the commands of those devices that are directly attached to the master 12 as opposed to being attached to a slave 14 which is, in turn, attached to the master 12.

All the other controllers, which for purposes herein, are referred to as slaves 14, include the lexicon for the devices that are directly connected thereto. For example, in FIG. 1, one slave includes the lexicon for the control commands and the select commands for a robotic arm and an operating table. This way, that controller can have a microphone plugged into the VCI which is included in the unit and it may serve as a solo unit. Or, depending upon the configuration of the control system 10, it may actually server as a master. The entire system 10 is configurable at startup and as such is expandable. Every controller preferably includes a VCI.

The decoder 40 additionally contains a language model. This term is well-known on the art and will be explained further hereinbelow. In essence, certain words may be validly said in certain orders. The language model is implemented by developing a network representing all the valid possibilities of word combinations and decoding the extracted vectors along each path in the network. Whichever path has the highest probability of matching the incoming speech, the information associated with that path is selected by the decoder 40. It is to additionally be appreciated that to carry out the present invention, a silence path is available and an unrecognized command path is provided as well. As such, even though a user speaks, if valid commands are not given, the system 10 will not respond.

Figure 5:
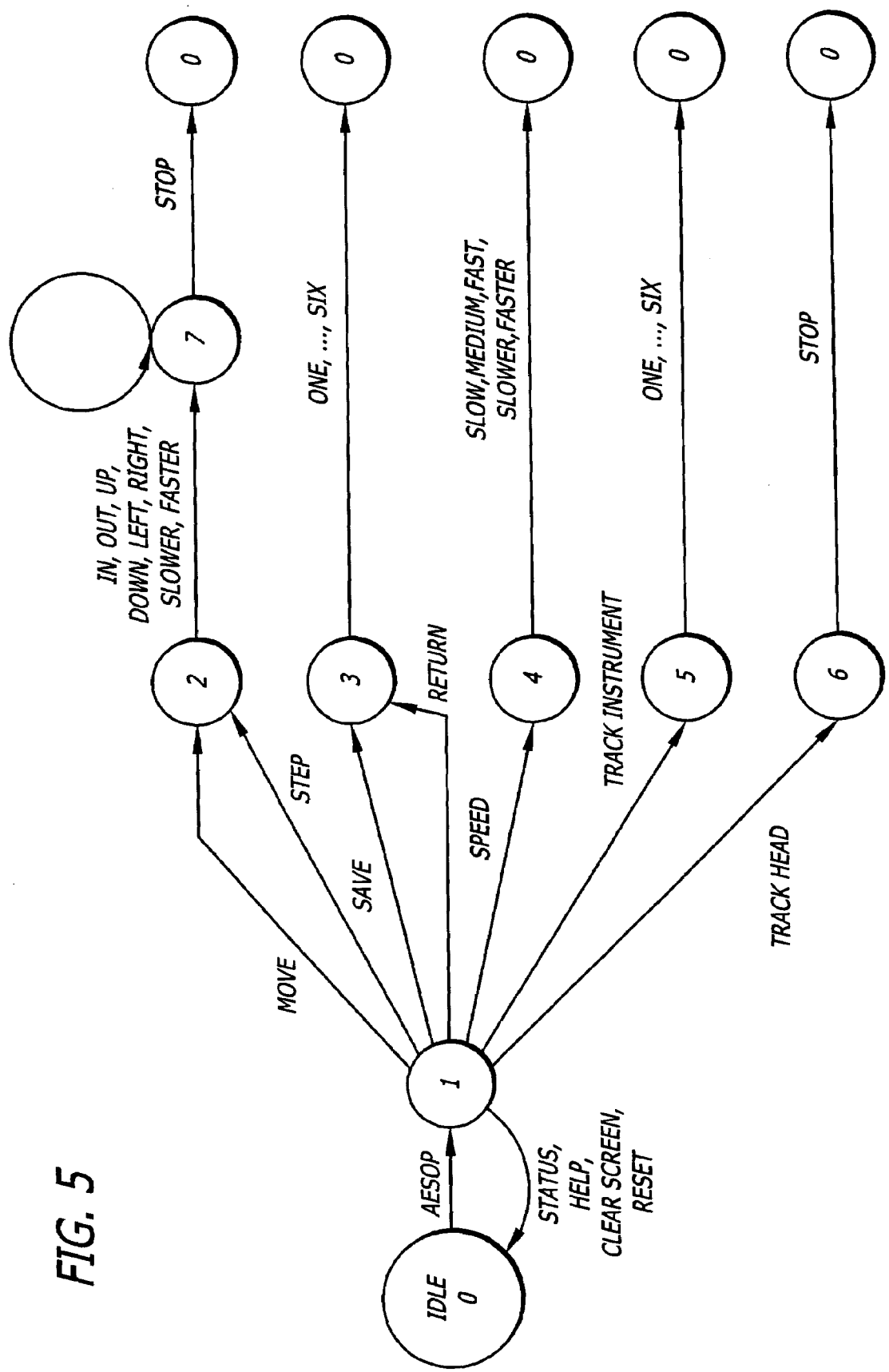
FIG. 5 is an exemplary tree diagram of a grammar for operating a device in accordance with the present invention.

FIG. 5 sets out one exemplary language model for the proper operation of the robotic arm 20. Such language models are developed for each device in electrical communication with the master controller 12. Once again, a device may be in wireless communication with the master controller 12. It is preferable to store the language models for each device in their respective controller. For example, if a device is directly connected to a slave 14 then the control language model (that language model containing the language used to control the device) for the device is stored in the slave VCI. If the device is directly connected to the master 12 then the control language model is included in the VCI of the master 12. It is to be appreciated that the select language model must be stored in the master 12 for all the possible devices that may be directly connected to the master 12 as opposed to being connected to a slave. As such, depending upon what devices are connected to the system at any given time, a user may select from any of the connected devices. If a device is not connected, the system will recognize this upon startup and will not attempt to access the device as it is not there. This will be discussed in more detail hereinbelow.

If a device is connected directly to the master controller 12, then it is preferable to store the language model for controlling the device either in the VCI itself, or in the transportable memory 45. The advantages of this configuration are set out hereinbelow with respect to the startup of the control system 10.

If a select command is given for a device that is directly connected to the master 12, then the information is passed to the decoder in the master 12 and the decoder 40 generates a packet 52 of information. The packet includes the address of the device to be operated, a code representing the specific operation, and a checksum to ensure that as the packet 52 is transferred over various busses, the data does not become corrupted. Such information packaging is well-known although the specific package set out hereinabove has heretofore not been utilized to control one of a plurality of medical devices. Data checking using a checksum is also well-known in the art.

The decoder 40, upon decoding a valid selection command, activates the address of the device which has been stored in a lookup table and is related to the device. This is accomplished as follows. At startup every controller, whether the master 12 or a slave 14 knows the addresses of its communication ports. It sends a query to each communication port to see if a device is connected thereto. If so, an adapter connected to the device specifies the name of the device and an indication that it is functioning properly. Such adapters are well known in the electrical arts and as such will not be further discussed herein. Every slave controller establishes a lookup table of addresses and associated device codes or names. The device codes or names are transmitted to the master 12 which includes all the devices and the corresponding address of the port to which the associated slave controller is connected to the master 12.

The addresses of all devices available are initially stored in a memory associated with the VCI such that a multiplexer may be used to activate a specific address or make that address accessible. In this fashion, once the master 12 receives a valid selection command, which it is able to identify, it then routes all the control commands to the VCI of the appropriate slave controller in the case where the device selected is connected to a slave controller. If the selected device is connected directly to the master 12 then the control commands are fed through the decoder 40 of the master 12 and the control information packet is produced and sent to the device via the central processor 44 of the master 12. In this fashion, the VCI of a slave is fed control signals and processes those signals as though they were received from the A/D converter, which is where the input to the slave is routed. Every slave can be attached to one master, and that master, can, in turn be attached to another master, thus providing a daisychain of slaves all of which are connected to one master having a microphone attached thereto.

Figure 4:
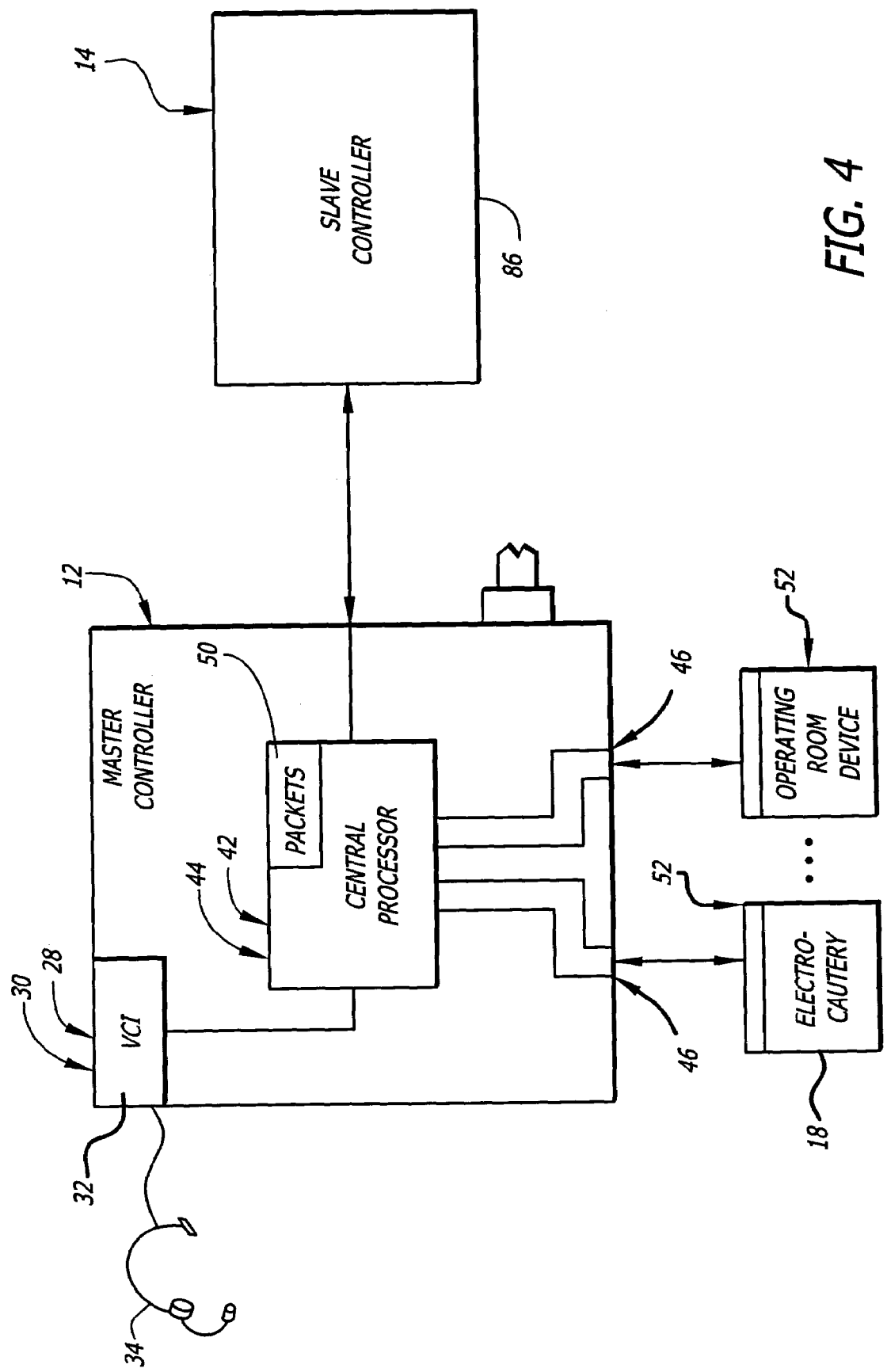
FIG. 4 is a schematic diagram of a master controller in accordance with a the present invention.

In addition to the VCI 32, the master controller 12 comprises means 42 for routing control signals to a device specified by a selection command received at the VCI 32. FIG. 4 depicts the master controller 12 having one slave controller 14 and two medical devices in electrical communication therewith. The master controller includes the VCI 32 as well as the means 42 for routing control signals. Once the speech has been extracted and decoded into either a selection command, or a control command, the specific command is transmitted to the Central Processor 44 of the master controller 12.

In the preferred embodiment, the means 42 for routing control signals is incorporated into the central processor 44 of the master controller 12. The means 42 for routing is essentially an addressable multiplexer and has a memory of the addresses for each device and their associated one of the plurality of communication ports 46 to which they are connected. If the addresses are stored in the decoder 40, then the central processor 44 will be in communication with that memory.

The means 42 for routing, takes the packet 50 of information or the control signal, if the information is to be sent to a slave 14, checks which of the plurality of communication ports 46 it is to direct the information to and then directs the information to the desired one of the plurality 46 of ports.

The addresses and their associated ports are uploaded into the master 12 upon startup of the system. This procedure is embedded in the software and such a procedure is well-known in the art.

For example, in FIG. 4, an electrocautery device 18 transmits an address to the master controller 12. The address is received at a one of a plurality of communication ports 46, the address is saved in the memory along with the associated communication port number. It is to be appreciated that the valid selection commands are stored on the transportable memory. For devices directly connected to the master, the language model may be stored in a memory in the master 12 or in the transportable memory. Language models are stored in associated slaves for devices that are directly connected to a slave 14. In this fashion, upon startup, the master 12 knows all devices that are connected to the system, as each slave sends to the master the addresses of each device and the name (i.e. coded phonemes that constitute the device) of the device. The names of the devices are uploaded into the master so that the validity of selection commands may take place in the master 12. However, language models for the validity of control commands are not transmitted to the master 12 as this would take much time and slow the control system 10 down. Therefore, the master controller 12 actually contains a subset of the grammar necessary to operate the devices in connection therewith, but that language model is limited to only the device names. The information regarding valid sequences of control commands (i.e. their control language model) is stored on each slave controller to which they are connected. Of course, if the device 14 is directly connected to the master, then the language model is stored at the master 12 as described hereinabove.

The control system 10 in accordance with the present invention provides a way to configure and reconfigure an operating room in a very simple fashion. Additionally, it is to be appreciated that the system 10 provides an intuitive interface whereby a user can select a device to control and then subsequently control that device. The system checks to ensure that control commands received for a specific device are valid.

Additionally, the system 10 requires the inclusion of adapters 52 placed intermediate a specific one of the plurality of devices 16 and a slave or the master 12. The adapters 52 transmit signals to their respective slave 14 or master 12 indicative of the address of the device, and translate control signals sent from the controller to which they are connected to signals understood by the particular device for which they are intended. Such adapters are easily constructed and are well-known in the art. Additionally, such adapters may be included either in the respective slave 14 or master 12 or attached to the particular one of the plurality of devices 16 itself. There is substantial advantage to attaching the adapters 52 to the devices 16 as then the devices may be attached to any port, whereas, if the adapters are attached interior the controller 12, 14, the specific device for which they were designed must be attached to the specific one of the plurality of communication ports 46.

If new devices are added to the system, or if improvements or upgrades are made to the system software, such changes may be incorporated into a PCMCIA format card, such as the card that stores the user voice models. The card may be inserted into the same interface, however, system software may be uploaded into the master to make the upgrade without having to disassemble the master. This is accomplished by incorporating a serial interface on the PCMCIA format card. As such, the central processor 44 additionally checks upon startup whether there is a system upgrade to be made by checking the data being supplied by the PCMCIA format card. Checking the activity of a serial interface is well known, however it is not heretofore known to incorporate a serial interface on a single PCMCIA format card. Therefore, the combination is seen to be novel. Additionally, it is heretofore not known to incorporate voice models on such a PCMCIA format card.

Each of the at least one slave 14 is substantially similar to the master controller 12. And, each of the plurality of slaves 14 may include the full VCI so that each slave 14 can operate as a master. Alternatively, although not preferred, the slaves may not include the feature extractor, and only contain a subset of the language model (i.e. control commands) relating to the operation of each specific device. This is all that may be necessary in the slave because the slave receives from the master controller the specific address a command is to be sent and that it is in fact a command. Therefore, the slave only needs to check to ensure that it is a valid command for the specific device. In this fashion, devices may be directly connected to the master, or they may be connected to a slave which is in communication with the master 12.

Finally, the system 10 may include output means including a video monitor 86 and a speaker 88. The speaker may be incorporated into the VCI 32 via a D/A converter 90 such that the system may communicate to the user any errors committed by the user in operating or selecting a specific device. Additionally, the output means may communicate system errors or the malfunction of a specific device. Such information is included in each specific adapter and is specific to the device attached to the adapter. It is to be appreciated that such communications would be transmitted to the master where they would be either auditorially or visually displayed. The system and controller in accordance with the invention may additionally include a foot controller, a hand controller or other well-known controllers. Each of these controllers may be used to control any of the devices connected to the master or a slave, as is described in the patent application incorporated herein by reference. As such, the VCI may only be used to select certain devices, and once selected the device may be controlled via one of the well-known controllers. Ultimately, the flexibility of such a system can reduce costs and increase the safety of surgical procedures.

While certain exemplary embodiments of the present invention have been described and shown on the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. As such, what is claimed is:

What is claimed is:

1. An operating room voice command system comprising:
a first medical device having a first device lexicon of verbal device commands associated therewith;
a second medical device having a second device lexicon of verbal device commands associated therewith; and
a control system in electrical communication with the first medical device and the second medical device, the control system having a voice interface for receiving a verbal device selection command included in a device selection lexicon, the device selection lexicon including a first device selection command and a second device selection command, the control system directing a command signal to a selected device in response to the verbal device selection command, the selected device being either the first medical device or the second medical device, the voice interface also for receiving a verbal device command associated with the selected device, the command signal corresponding to the device command, the control system identifying the device command from among the first device lexicon when the selected device is the first medical device, and the control system identifying the device command from among the second device lexicon when the selected device is the second medical device.

2. The operating room voice command system of claim 1, wherein the first medical device includes an operating room lighting system.

3. The operating room voice command system of claim 2, wherein the first device lexicon includes room lighting commands.

4. The operating room voice command system of claim 2, wherein the second medical device includes an operating room table.

5. The operating room voice command system of claim 1, wherein the second medical device includes an operating room table.

6. The operating room voice command system of claim 1, wherein the first medical device includes at least one of an insufflator, a robot arm for holding and manipulating an endoscope, and a laser.

7. The operating room voice command system of claim 1, wherein the voice interface identifies speech of a user as a member selected from the group consisting of:
 a device selection command,
 a device command for the selected device, and
 other speech.

8. The operating room voice command system of claim 7, wherein the voice interface differentiates between other speech and device commands using the lexicon associated with the selected device, and wherein the lexicon associated with the selected device is stored on a memory of the selected device.

9. The operating room voice command system of claim 8, wherein the voice interface comprises a master controller with a muter controller memory, the first medical device has a first slave controller with a first memory and the second medical device has a second slave controller with a second memory, and the voice interface differentiates between different device selection commands of the device selection lexicon while the device selection lexicon is stored on the master controller memory.

10. The operating room voice command system of claim 1, wherein the control system identifies a plurality of devices in electrical or wireless communication therewith, the plurality of devices including the first medical device and the second medical device, and wherein the control system determines the device selection lexicon in response to the identified devices, the device selection lexicon including a device selection command associated with each identified device.

11. The operating room voice command system of claim 10, wherein the control system is configured to identify the plurality of devices at a start-up.

12. The operating room voice command system of claim 1, further comprising a third medical device having a third device lexicon of verbal commands associated therewith, the voice interface capable of transmitting command signals to the third medical device corresponding with verbal commands of the third device lexicon when the third medical device is in electrical communication with the control system, wherein the third medical device is not in electrical communication with the control system and the control system does not generate command signals corresponding to the third device lexicon.

13. The operating room voice command system of claim 1, further comprising a video monitor coupled to the control system, the video monitor displaying communications with the selected device.

* * * * *